US006805881B1

(12) United States Patent
Kanikanti et al.

(10) Patent No.: US 6,805,881 B1
(45) Date of Patent: Oct. 19, 2004

(54) MULTIPLE UNIT CONTROLLED FOOD EFFECT-INDEPENDENT RELEASE PHARMACEUTICAL PREPARATIONS AND METHOD FOR PREPARING THE SAME

(75) Inventors: Venkata-Rangarao Kanikanti, Leverkusen (DE); Roland Rupp, Bergish Gladbach (DE); Erich Brendel, Solingen (DE); Claus Weisemann, Apex, NC (US); Ernst Chantraine, Walnut Creek, CA (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/787,229

(22) PCT Filed: Sep. 17, 1999

(86) PCT No.: PCT/EP99/06882

§ 371 (c)(1),
(2), (4) Date: Mar. 23, 2001

(87) PCT Pub. No.: WO00/16748

PCT Pub. Date: Mar. 30, 2000

(30) Foreign Application Priority Data

Sep. 18, 1998 (DE) .......................................... 198 42 753

(51) Int. Cl.[7] .............................. A61K 9/14; A61K 9/48; A61K 9/52; A61K 9/20; A61K 9/22
(52) U.S. Cl. ........................ 424/488; 424/451; 424/457; 424/458; 424/464; 424/468; 424/474
(58) Field of Search .................................. 424/488, 457, 424/458, 464, 468, 474, 451; 414/451

(56) References Cited

U.S. PATENT DOCUMENTS

| | | | |
|---|---|---|---|
| 4,203,400 A | 5/1980 | Yorioka ........................ 123/119 |
| 4,226,849 A | * 10/1980 | Schor | |
| 4,327,725 A | 5/1982 | Cortese et al. ............... 128/260 |
| 4,369,172 A | * 1/1983 | Schor et al. | |
| 4,389,393 A | * 6/1983 | Schor et al. | |
| 4,449,983 A | 5/1984 | Cortese et al. ............... 604/892 |
| 4,801,460 A | 1/1989 | Goertz et al. ................ 424/465 |
| 4,880,585 A | 11/1989 | Klimesch et al. ............ 264/141 |
| 4,892,741 A | 1/1990 | Ohm et al. .................... 424/479 |
| 4,940,587 A | * 7/1990 | Jenkins et al. | |
| 5,073,379 A | 12/1991 | Klimesch et al. ............ 424/467 |
| 5,234,691 A | 8/1993 | Uemura et al. ............... 424/456 |
| 5,456,923 A | 10/1995 | Nakamichi et al. .......... 424/489 |
| 5,552,159 A | 9/1996 | Mueller et al. ............... 424/464 |
| 5,783,215 A | * 7/1998 | Arwidsson et al. | |

FOREIGN PATENT DOCUMENTS

| | | | | |
|---|---|---|---|---|
| EP | 0 205 282 B1 | * | 5/1986 | |
| EP | 0205282 | | 9/1995 | ............ A61K/9/22 |
| WO | 9528147 | | 10/1995 | |
| WO | 9611674 | | 4/1996 | |
| WO | 9625149 | | 8/1996 | |

OTHER PUBLICATIONS

Acquier, R., "Approche due comportement des hydroxypropylcelluloses en presence d'eau, en fonction de la masse moleculaire et de la concentration", Pharmaceutica Acta Helvetiae, 62(11): 315–320 (1992).
Acquier, R., "Hydroxypropyl cellulose et liberation des principes actifs 1. Influence de la masse moleculaire du polymere et de sa concentration", S.T.P. Pharma Sciences, 2(6):469–474 (1992).
Abrahamsson, B., Alpsten, M., Bake, B., Jonson, U. E., Eriksson–Lepkowska, M., and Larsson, A., "Drug Absorption from Nifedipine Hydrophilic Matrix Extended–Release (ER) Table–Comparison with an Osmotic Pump Tablet and Effect of Food", J. Controlled Ref., 52: 301–310 (1998).
Abrahamsson, B., Alpsten, M., Bake, B., Larsson, A., and Sjogren, J., "In vitro and in vivo erosion of two different hydrophilic gel matrix tablets", Eur. J. Pharm. Biopharm., 46: 69–75 (1998).
Colombo, I., and Vecchio, C., "An evaluation of the physical properties of small matrices compressed by an instrument rotary press", Acta Technologiae et Legis Medicamenti, vol. III, No. 3, pp. 137–145 (Dec. 1992).
Lindner, W. D., Mockel, J. E., and Lippold, B. C., "Controlled Release of Drugs from Hydrocolloid Embeddings", Pharmazie, 51: 263–272 (1996).

* cited by examiner

Primary Examiner—Thurman K. Page
Assistant Examiner—Humera N. Sheikh

(57) ABSTRACT

The present invention relates to orally administrable multiple-unit sustained-release dose forms having controlled agitation-independent release of active compound and processes for their production using a selected erodable hydrophilic polymer (HPC) and a limitation of the maximum size of the active compound-containing polymer particles to ≦3 mm.

12 Claims, No Drawings

MULTIPLE UNIT CONTROLLED FOOD EFFECT-INDEPENDENT RELEASE PHARMACEUTICAL PREPARATIONS AND METHOD FOR PREPARING THE SAME

The present invention relates to orally administrable multiple-unit sustained-release dose forms having controlled and agitation-independent release and processes for their production using a selected erodable hydrophilic polymer.

For many medicaments, it is desirable that they guarantee a controlled, long-lasting and uniform release of the active compound after administration once daily. In this way, the desired plasma concentration can be maintained over a relatively long period without great variations and thus the medicament safety and the patient compliance are increased. Formulations which release the active compound over a defined period in this manner are called sustained-release formulations. Various techniques for their production are already known.

Very often, single-unit matrix tablets which contain the active compound in a matrix of polymers and some pharmaceutical excipients are employed for this purpose. The polymer can either be hydrophilic or hydrophobic or a mixture thereof. Meanwhile, matrix tablets containing hydrophilic polymers have become very popular, since these are comparatively inexpensive, non-toxic, processable in conventional plants, etc.

A further method is the coating of preparation forms with buffered or pH-dependent coatings which are intended to guarantee a controlled release in certain areas of the gastrointestinal tract.

While the erosion matrix tablets are susceptible to mechanical stress, in particular hydrodynamic stresses, the pH-controlled formulations are susceptible to pH changes in the gastrointestinal tract. While the tablet moves through the gastrointestinal tract, both the pH and the mechanical stress vary, in particular also as a function of the nature and amount of the filling of the stomach and of the digestive tract. This dependence of the active compound release is called the "agitation dependence" or the "food effect". It is seen that the release rate of most sustained-release formulations is dependent on the food intake and thus different profiles of action occur depending on whether the medicament is taken before, during or after a meal.

There have been numerous attempts to exclude or to minimize the undesirable variability of this "food effect". For erosion-controlled preparations, an approximately agitation-independent single-unit system has been described which, however, is technically very complicated and therefore impracticable (cf. W. D. Lindner et al. Farm., 51 (1996) 263). As a further possibility of an agitation-independent preparation, a single-unit osmotic pump system has been described and in some cases successfully marketed. Here, the active compound is squeezed outwards through defined openings or pores of a chamber, the squeezing pressure being produced by a swelling polymer whose water absorption is osmotically controlled (cf. U.S. Pat. Nos. 4,449,983, 4,203,400 and 4,327,725).

The problems and disadvantages of the previously proposed and employed agitation-independent sustained-release formulations are known and presented, inter alia, in the description of EP 0 425 298.A2. According to this application, it is attempted to achieve the agitation independence of salt-forming active compounds by means of different coatings with poorly soluble polymers. The disadvantages of this process likewise lie in the technically complicated process measures and in the fact that only certain salt-forming and thus easily soluble active compounds can be employed.

Multiple-unit formulations are designated as those formulations which, in contrast to so-called single-unit formulations such as tablets, consist of a number of small particles, e.g. pellets, granules, minitablets or grains which are contained, for example, in a capsule. In the gastrointestinal tract, these particles are then present independently of one another. Such multiple-unit formulations have a number of advantages in comparison to single-unit formulations. They provide for a more uniform absorption of the active compound and for smaller inter- and intraindividual variations of the pharmacokinetic profiles. Furthermore, different active compounds and dosages can thus be simply inserted, for example, into capsules. These formulations can thus be tailored to the different medicinal requirements without a great outlay.

The object of the present invention is to be seen as making available agitation-independent multiple unit sustained-release formulations, i.e. formulations without an interfering food effect, which can be produced in a simple manner for all types of active compounds, in particular for poorly soluble active compounds.

Multiple-unit sustained-release formulations according to the present invention are formulations which, in the USP paddle test using apparatus II, release 80% of the active compound within 4 to 14 hours, preferably within 6 to 12 hours, relative to the total amount of active compound in the formulation.

Agitation-independent formulations according to the present invention are those which, in the USP XXII paddle test with 900 ml of release medium, pH 6.8 at a stirren speed of 50 rpm and of 150 rpm, have a maximum release difference of ±10%, preferably ±5%.

The stirren speed of the paddle test according to USP was selected with regard to the publication B. Abrahamsson et al., Eur. J. Pharm. Sci., 46 (1998) 69, according to which the mechanical stress of a tablet in the gastrointestinal tract is to be compared, for example, with the conditions which correspond to a stirring motion in the paddle test at up to about 150 rpm.

This object can be achieved according to the invention in that a) the hydrophilic polymer employed is hydroxypropyl-cellulose (HPC) having an average molecular weight of 250000 to 1200000, preferably 350000 to 1150000, in an amount from 40 to 95% by weight, preferably 45 to 90% by weight, based on the active compound-polymer mixture, and a molar degree of substitution of $\geq 3$ as a release-sustaining erosion material and b) the active compound-polymer combination is converted into small particles such as pellets, granules or minitablets having a maximum diameter of 0.2 to 3.0 mm, preferably of 0.5 to 2 mm.

HPC having an average molecular weight of 700000 to 1200000, preferably 850000 to 1150000, can also be employed.

Maximum diameter is here understood as meaning the greatest longitudinal dimension of the particle; according to the invention it is 0.2 to 3 mm.

If desired, the miniparticles can be lacquered and further customary pharmaceutical excipients can also be added.

These sustained-release miniparticles can be produced and administered in a simple manner in the desired dose units as multiple-unit sustained-release dose forms, e.g. in hard gelatin capsules, as sachets or are modified to give tablets which decompose into the miniparticles again immediately after administration and thus behave like a multiple-unit dose form.

With knowledge of the prior art, it was not obvious that, as a result of the selection of the abovementioned erodable hydrophilic polymer HPC and simultaneous limitation of the maximum size of the active compound-containing polymer particles to at most 3 mm diameter, an agitation-independent sustained-release formulation can be produced. It was rather to be expected that erodable hydrophilic polymers especially would exhibit a particularly strong agitation effect or food effect. It is known, for example, that nifedipine-containing matrix tablets having diameters of 9 or 10 mm, which contain HPC or HPMC (hydroxypropylmethylcellulose) as hydrophilic polymer, are strongly agitation-dependent and exhibit a strong food effect (cf. Adalat CC®; EP 0 299 211 and B. Abrahamsson et al., J. Controlled Rel., 52 (1998) 301).

On the other hand, minitablets for oral administration have been known and described for some time (cf. Colombo et al., Acta Technol. Legis. med. 1992, 3 (3), 137). However, it was previously not known that the particles according to the invention having a maximum diameter of 3 mm are agitation-independent sustained-release formulations.

To achieve the object according to the invention, the combination of both elements a) and b) is necessary. Some experiments with minierosion tablets which contain nifedipine as active compound and which do have a diameter of 2 mm, but contain a mixture of hydroxyethylcellulose (HEC) and hydroxypropylmethylcellulose (HPMC) as erodable polymer, show a significant agitation dependence.

Surprisingly, it has been found that, as a result of the combination of the selection of the erodable hydrophilic polymer HPC and the reduction of the size of the minipar-ticles to be employed to at most 3 mm diameter, agitation-independent multiple-unit sustained-release formulations can be obtained in a simple and effective manner.

According to informative tests, the formulations according to the invention showed virtually no food dependence.

The pellets, granules, minitablets or grains used according to the invention are produced according to customary methods. In addition to the conventional formulation methods, in which HPC is granulated with the active compound and, if appropriate, further excipients using water or organic solvents, the use of melt extrusion methods can also be employed advantageously. Such melt extrusion methods have been known for a long time. Variations of this melt extrusion are also proposed in the more recent patent literature (cf. DE 195 04 831.8, EP 240 904, U.S. Pat. No. 5,456,923, EP 544 144 and in particular WO 96/25149).

Many of the previously known methods of melt extrusion have a number of disadvantages compared with the methods employable according to the invention. Thus, for the production of an extrudate, at least two polymers, e.g. a water-soluble polymer and a water-insoluble polymer, are often used. Owing to the necessity of additional plasticizers or other excipients, the ratio excipient/pharmaceutical can be unfavourably influenced, so that the finished product is very voluminous and also expensive. According to the present invention, the agitation- and food-independent formulations can be obtained even by simple mixing and extrusion of the desired active compound with HPC.

If desired, further excipients can of course also be employed for the multiple-unit sustained-release formulations according to the invention, e.g. magnesium stearate or film coatings or lacquers which prevent the sticking together of the particles. These excipients, however, have no direct influence on the sustained-release action of the preparation according to the invention, which is agitation-independent or has no food effect.

It is also possible to employ for the preparation of the minitablets in addition to the essential polymer HPC further hydrophilic and water-insoluble polymers, e.g. poly-methacrylate esters. An example is the known ammonio methacrylate copolymer type B (Eudragit® RS PO).

The present invention also relates to processes for the production of multiple-unit sustained-release dose forms, characterized in that at least one therapeutically active substance and HPC having an average MW of 250000 to 1200000 as a hydrophilic thermoplastic, but pharmaceutically acceptable polymer and also, if appropriate, further customary pharmaceutical excipients which, however, do not contribute to the sustained-release effect, are mixed, granulated and tableted or mixed, extruded and granulated to give particles having a maximum particle diameter of 3 mm and these are then converted into a suitable oral administration form.

In the extrusion process, therapeutically active pharmaceuticals and the polymer are conveyed either simultaneously, without prior mixing, or as a mixture, after prior mixing, into a normal extruder, preferentially a double-screw extruder, which has been heated beforehand to a temperature at which the polymer and the pharmaceutical are not degraded. The temperature range at the outlet nozzle of the extruder here is 50 to 220° C., preferably 80 to 210° C. and particularly 100–180° C. In the area of the product inlet into the extruder, the temperature is around 25° C. The temperature in the intermediate area of the extruder is between the temperature in the product inlet area of the extruder and the temperature at the outlet nozzle of the extruder.

The homogeneous mixture softens during passage through the extruder and is pressed at the end through a plate which contains at least one nozzle having a defined diameter of about 0.2 to 3.0 mm, preferably of 0.5 to 2.0 mm. The extruded strands, which on emergence from the extruder nozzle are still soft and rapidly become solid at room temperature, are cut to give granules having a particle diameter of about 0.2 to 3 mm, preferably 0.5 to 2 mm, directly after their emergence. Alternatively, the extruded strands are immediately (on-line) granulated (e.g. water-ring granulation or underwater granulation or air granulation) or immediately cut into pieces. Air granulation is preferred. The extrudates obtained can be filled directly into hard gelatin capsules. As a particular embodiment, it has proved advantageous additionally to lacquer the extrudates obtained before filling them into gelatin capsules, preferably using a water-insoluble but water-permeable and non-gel-forming polymer.

This sustained-release dose form according to the present invention is not susceptible to mechanical stress or hydro-dynamic stress in the gastrointestinal tract; the rate of the active compound release therefore does not depend on the mechanical stress and the hydrodynamic stress to which the product is exposed and is independent of the degree of filling of the stomach. The sustained-release dose form thus exhibits no food effect.

The lacquered extrudates can be compressed with conventional excipients (e.g. microcrystalline cellulose, Ac-Di-Sol® etc.) to give tablets. These tablets decompose rapidly after their administration, so that the tablet behaves as a multi-unit dose form.

The formulation according to the present invention can also be produced using known tableting processes, in which the ingredients are granulated, for example, in a known manner, made glidable and compressed to give microtablets of a diameter of ≦3 mm, preferably of ≦2 mm.

In contrast to the formulations according to the prior art, the agitation-independent sustained release is achieved, as already mentioned, in the present invention by the combination a) of the polymer HPC used and b) the maximum diameter, whilst the coating only serves to protect the dose form from sticking.

The active compounds used can be any desired orally administrable pharmaceuticals, e.g. anti-infectives, circulatory agents, antimycotics, antidepressants, antidementia agents, antiepileptics, anti-inflammatories, analgesics, antiasthmatics, antithrombotics, antitumour agents, antimalaria agents, non-steroidal antiinflammatory agents (NSAID), diuretics, antiarrhythmics, blood sugar-lowering agents, ACE inhibitors, sedatives, decongestants, antihistamines or hypolipidaemics. Hypolipidaemics can be, inter alia, Apo B inhibitors or MTP inhibitors. Of particular interest are the Apo B inhibitors according to EP 705 831, to which reference is expressly made here. Of very particular interest is the substance 2-cyclopentyl-2-[4-(2,4-dimethylpyrido[2,3-b]indol-9-yl-methyl)-phenyl]-N-(2-hydroxy-1-phenyl-ethyl)acetamide. For the purposes of the present invention, only those pharmaceuticals are incorporated which do not decompose under the temperatures and processing conditions. The amount of active compound to be administered per dose unit can be varied depending on the nature of the pharmaceutical and the release rate. It has proved advantageous to employ 0.8 to 10 parts by weight, preferably 1 to 5 parts by weight, of the gel-forming polymer to one part by weight of active compound.

In contrast to the previously known techniques, only a single polymer is needed for sustained release according to the present invention. The desired release rate is obtained by variation of the production parameters. The pharmaceutical release rate is, for example, influenced by the pharmaceutical concentration in the final product or by process parameters of the extrusion, such as the screw geometry, the extrusion rate, the extrusion temperature, the diameter and the surface area of the extrudate, the viscosity and molecular weight of the polymer, etc.

As already mentioned, further customary excipients can also be used which are customary in the production of solid dose forms in pharmacy and are known from the literature. None of these excipients is necessary, however, in order significantly to influence the desired retardation of the release of the pharmaceutical and the agitation independence according to the invention. These excipients rather only serve to make the process more flexible.

The extrudates or minitablets are optionally lacquered, for example, with pH-independent aqueous dispersions such as an ethylcellulose dispersion (e.g. Aquacoat EC 30 trade mark of FMC) or of a poly(ethyl acrylate, methyl methacrylate) 2:1 (e.g. Eudragit NE 30 D trade mark of Röhrn Pharma). Moreover, a plasticizer such as triethyl citrate or Tween 20 can be used in order that the lacquer film does not become brittle during storage. Magnesium stearate can additionally be incorporated into the lacquer suspension as an antiadhesive agent. HPMC serves as the pore former. The lacquer essentially has no influence on the release rate, except that a retardation of the commencement of release (lag time) can occur during the first 1–2 hours after the administration.

Typical lacquer suspensions for minitablets and extrudates which may be mentioned are: (all data in % by weight)

A. 30–60% (preferably 40%) of Eudragit® NE 30 D dispersion; 3–10% (preferably 5%) of HPMC 3 cP; 0.05–0.5% (preferably 0.1%) of Tween 20; 1–7.5% (preferably 2.5%) of magnesium stearate and completely deionized water to 100%.

B. 15–30% (preferably 25%) of Aquacoat® EC 30 D dispersion; 3–10% (preferably 4–5%) of HPMC 15 cP; 0.5–4% (preferably 2%) of triethyl citrate and completely deionized water to 100%.

The lacquer suspensions, for example, are prepared by first dissolving HPMC and the plasticizer separately in water and then mixing them with the dispersion of the film former. In the presence of magnesium stearate, this is dispersed in the aqueous solution of HPMC and plasticizer before the addition of the Eudragit NE 30 D dispersion.

The optionally lacquered particles of the active compound-polymer combination according to the invention, such as pellets, granules, minitablets or grains, can be filled into capsules, pressed to give tablets or further processed to give other known administration forms or finished medicaments according to customary methods.

The invention is illustrated in greater detail by means of the following examples.

INFLUENCE OF PADDLE AGITATION ON THE ACTIVE COMPOUND RELEASE

The active compound release from Examples 16 and 17 according to the invention and from the Comparison Example A over time was investigated in a USP XXII paddle test. It was seen here that in Examples 16 and 17 the active compound release at 50 and 150 revolutions per minute (rpm) lay apart by at most 5% over a period of 14 hours (i.e. up to complete release), whilst in Comparison Example A release differences of up to 50% occurred.

COMPARISON EXAMPLE A 19.4 parts by weight of hydroxypropylmethylcellulose (viscosity 100000 cP, type 2208) and 45.3 parts by weight of hydroxyethylcellulose (viscosity 15000 cP) are granulated with an aqueous suspension of nifedipine (30 parts by weight) and hydroxypropylcellulose (2 parts by weight) of a viscosity of <10 cP. The granules obtained are made glidable with magnesium stearate and compressed to give 2 mm minitablets of 6.4 mg. The minitablets are lacquered in a conventional manner with an aqueous dispersion of Eudragit NE 30 D, magnesium stearate, Tween 20®, hydroxypropylmethylcellulose 3 cP and water. Per kg of minitablets, 0.6 kg of lacquer suspension A is sprayed on. Some lacquered minitablets containing an equivalent of 30 mg of nifedipine are encapsulated.

WORKING EXAMPLES

Example 1

3 kg of the pharmaceutical nifedipine are mixed with 7 kg of highly viscous HPC (MW 400000 from Nippon Soda, Japan). The mixture is processed in a double-screw extruder with two outlet nozzles having a diameter of 2 mm. The material is extruded at a nozzle temperature of 150° C. The temperature of the various subunits in the extruder cylinder is adjusted to a temperature which lies at least approximately 10° C. below the nozzle temperature. The extrudate is cut into cylinders approximately 2 mm long and lacquered in a fluidized bed lacquering unit. Per kg of extrudate, 0.6 kg of the lacquer suspension A is sprayed on. The lacquering is carried out under customary conditions.

Example 2

Analogous to Example 1, but 2 kg of nifedipine are mixed with 8 kg of the same polymer type.

Example 3

Analogous to Example 1, but the nozzle temperature is 160° C.

Example 4

Analogous to Example 1, but the nozzle diameter is 1.4 mm.

Example 5

Analogous to Example 1, but the nozzle diameter is 0.8 mm.

Example 6

Analogous to Example 1, but the extruded strands were first cut into cylinders approximately 3 mm long.

Example 7

Analogous to Example 1, but the cylinders cut approximately 2 mm long were not lacquered.

Example 8

Analogous to Example 1, but the nozzle temperature is 140° C.

Example 9

Analogous to Example 1, but the polymer used is HPC having an average molecular weight of about 850000 (Hercules, USA).

Example 10

Analogous to Example 1, but the polymer used is HPC having an average molecular weight of about 1000000 (Hercules, USA).

Example 11

Analogous to Example 1, but the pharmaceutical used is nisoldipine.

Example 12

Analogous to Example 1, but the pharmaceutical used is nimodipine, HPC (MW 400000, Nippon Soda, Japan) is employed, and the nozzle temperature is 110° C.

Example 13

The same composition as in Example 1 is extruded under the same extrusion conditions in a commercially obtainable extrusion and granulation apparatus and then immediately granulated by means of the water ring process and dried. The resulting extrudate was slightly rounded and, as a result, more easily processable.

Example 14

The same composition as in Example 1 is extruded in a commercially obtainable extrusion apparatus having a nozzle plate of 40×0.8 mm or 36×1.3 mm drillings, and then immediately on-line granulated and dried by air granulation. The resulting extrudates were more easily processable. The granules were lacquered as in Example 1.

Example 15

The same composition as in Example 1 is extruded through an extruder with outlet nozzles having a diameter of 1 mm, and the extruded strand is cooled by spraying with water and immediately granulated and dried. The extrudates obtained are further processed as described in Example 1.

Example 16

250 parts (by weight) of hydroxypropylcellulose (MW 1000000; viscosity 1500 to 3000 cP (1% w/v; 25° C.)) are granulated with an aqueous suspension of nifedipine (30 parts) and hydroxypropylcellulose (2 parts). The resulting granules are made glidable with magnesium stearate (1.5 parts) and compressed to give 2 mm minitablets of 6.5 mg. The minitablets are lacquered in a conventional manner with an aqueous dispersion of Eudragit NE 30 D, magnesium stearate, Tween 20®, hydroxypropylmethylcellulose 3 cP and water. Per kg of minitablets, 0.6 kg of lacquer suspension A is sprayed on. Some lacquered minitablets are encapsulated with an equivalent of 30 mg of nifedipine.

Example 17

Hydroxypropylcellulose corresponding to Example 16 (42.6 parts) is mixed with Eudragit® RS PO (40.8 parts) and granulated with an aqueous suspension of nifedipine (30 parts) and hydroxypropylcellulose (2 parts) of a viscosity of <10 cP. The resulting granules are made capable of gliding with magnesium stearate (1.5 parts) and compressed to give 2 mm minitablets of 6.5 mg. The minitablets (2 mm diameter) are lacquered analogously to Example 16.

Example 18

1 kg of 2-cyclopentyl-2-[4-(2,4-dimethyl-pyrido[2,3-b]indol-9-yl-methyl)-phenyl]-N-(2-hydroxy-1-phenyl-ethyl) acetamide are mixed with 2 kg of HPC (MW 250000–400000, Nippon Soda, Japan). The mixture is processed in a double-screw extruder with two outlet nozzles having a diameter of 2 mm. The material is extruded at a nozzle temperature of 215° C. The extrudate is cut into cylinders approximately 2 mm long and lacquered in a fluidized bed lacquering unit analogously to Example 1.

If bit expressly stated otherwise, the term "parts" in the present application should always be understood as meaning "parts by weight".

What is claimed is:

1. A process for the production of an orally administratable multiple-unit sustained-release pharmaceutical composition having controlled agitation-independent release, consisting essentially of the steps of (a) combining hydroxypropylcellulose polymer having a molecular weight of 250000 to 1200000 and a molar degree of substitution of at least 3 in an amount from 40 to 95% by weight with a pharmaceutically active compound and optionally with one or more pharmaceutically acceptable additional polymers and/or excipients which do not contribute significantly to a sustained-release effect, to obtain a mixture of containing said hydroxypropyl cellulose polymer and said active compound; (b) converting said mixture into particles having a diameter of 0.2 to 3.0 mm; (c) optionally lacquering said particles, and (d) incorporating said particles into an orally administratable multi-unit sustained release dosage form.

2. The process according to claim 1, wherein said hydroxypropylcellulose polymer is employed in an amount from 45 to 90% by weight.

3. The process according to claim 1, wherein said hydroxypropylcellulose polymer has an average molecular weight of 350000 to 1150000.

4. The process according to claim 1, wherein said particles have a maximum diameter of 0.5 to 2 mm.

5. The process according to claim 1, wherein said particles are produced by melt extrusion and/or granulation.

6. The process according to claim 1, wherein said particles are converted into said orally administratable pharmaceutical composition by conventional tableting methods.

7. The process according to claim 1, wherein said particles are in the form of pellets, granules, minitablets or grains.

8. A pharmaceutical composition consisting essentially of a mixture of hydroxypropylcellulose polymer and a pharmaceutically active compound and optionally one or more pharmaceutically acceptable additional polymers and/or excipients which do not contribute significantly to a sustained-release effect, wherein said hydroxypropylcellulose polymer has a molecular weight of between 250,000 and 1,200,000 and a molar degree of substitution of $\geq 3$ and is 40–95% by weight of said mixture and further wherein said mixture is granulated to particles having a diameter of between 0.2 and 3.0 mm, said particles being optionally lacquered, and said composition being in a agitation independent, orally administratable multi unit, sustained release dosage form.

9. The pharmaceutical composition of claim 8, wherein said dosage form is selected from the group consisting of a capsule, a sachet and a tablet which decomposes into its constituent particles quickly after being administered.

10. The dose form of claim 9 wherein said dosage form is a capsule.

11. The process according to claim 1 wherein said orally administratable multi-unit sustained release dosage form is a capsule, a sachet, or a tablet which decomposes into its constituent particles quickly after being administered.

12. The process of claim 11 wherein said dosage form is a capsule.

* * * * *